US007568377B2

(12) United States Patent
Bhethanabotla et al.

(10) Patent No.: US 7,568,377 B2
(45) Date of Patent: Aug. 4, 2009

(54) HIGH FREQUENCY THICKNESS SHEAR MODE ACOUSTIC WAVE SENSOR FOR GAS AND ORGANIC VAPOR DETECTION

(75) Inventors: Venkat R. Bhethanabotla, Tampa, FL (US); Randolph D. Williams, Tampa, FL (US)

(73) Assignee: University of South Florida, Tampa, FL (US)

( * ) Notice: Subject to any disclaimer, the term of this patent is extended or adjusted under 35 U.S.C. 154(b) by 186 days.

(21) Appl. No.: 11/460,851

(22) Filed: Jul. 28, 2006

(65) Prior Publication Data

US 2009/0151428 A1 Jun. 18, 2009

Related U.S. Application Data

(60) Provisional application No. 60/703,371, filed on Jul. 28, 2005.

(51) Int. Cl.
*G01N 29/00* (2006.01)
(52) U.S. Cl. ........................... 73/24.06; 73/61.79
(58) Field of Classification Search ............... 73/61.79, 73/64.53, 24.01, 24.06
See application file for complete search history.

(56) References Cited

U.S. PATENT DOCUMENTS 3,164,004 A * 1/1965 King, Jr. ..................... 73/24.06

(Continued)

FOREIGN PATENT DOCUMENTS

WO   WO 2004072622 A1 * 8/2004

OTHER PUBLICATIONS

Micro Analytical Systems Department Technology—uChemLab. Sandia National Laboratories.

(Continued)

*Primary Examiner*—John Fitzgerald
(74) *Attorney, Agent, or Firm*—Michael M. McGaw; Smith & Hopen, P.A.

(57) ABSTRACT

A thickness shear mode (TSM) sensor having a visco-elastic polymer coating and a fundamental frequency greater than 20 MHz useful for organic vapor or gas detection. The TSM quartz resonators at a fundamental frequency of 96 MHz were evaluated for their performance in organic vapor sensing applications and results were compared with the performance of 10 and 20 MHz resonators. These devices were produced by chemical milling of AT-cut quartz. Seven test organic vapors were utilized at concentrations ranging from 0.2 volume percent to 13.7 volume percent in the vapor phase. In all cases, the rubbery polymer polyisobutylene was used as a sensing layer. Detailed results for various sensor parameters such as sensitivity, baseline noise and drift, limit of detection, response and recovery times, dynamic range, and repeatability for the 96 MHz device were compared with those for 10 and 20 MHz devices. The test case of benzene/polyisobutylene was chosen to make these detailed comparisons. The 96 MHz device was found to be more sensitive than the lower frequency devices. Device sensitivity was dependent on the benzene concentration. Response and recovery times were smaller for the 96 MHz device. Response times decreased with analyte concentration. Sensor response was in reasonable agreement with the perturbation model of Sauerbrey at lower concentrations and deviated at the higher concentrations for the 96 MHz device. Higher frequency TSM devices can be very useful as organic vapor sensors both in detection and process monitoring applications. These devices have the advantages of simpler electronics, easier design and fabrication, well-developed models and good baseline stability when compared to other acoustic wave devices.

17 Claims, 16 Drawing Sheets

U.S. PATENT DOCUMENTS

| | | | |
|---|---|---|---|
| 3,694,677 A | | 9/1972 | Gutwein et al. |
| 3,872,411 A | * | 3/1975 | Watanabe et al. ........... 333/187 |
| 3,891,872 A | * | 6/1975 | Nagata et al. ............... 310/320 |
| 4,221,986 A | * | 9/1980 | Besson ....................... 310/344 |
| 4,517,485 A | * | 5/1985 | Berte et al. ................. 310/320 |
| 4,656,707 A | * | 4/1987 | Berte et al. ................. 29/25.35 |
| 4,720,651 A | * | 1/1988 | Nakazawa et al. .......... 310/369 |
| 4,741,200 A | * | 5/1988 | Hammerle .................. 73/54.25 |
| 5,185,550 A | * | 2/1993 | Morita et al. ............... 310/344 |
| 5,201,215 A | * | 4/1993 | Granstaff et al. ........... 73/54.41 |
| 5,218,328 A | * | 6/1993 | Morita et al. ............... 333/187 |
| 5,235,240 A | * | 8/1993 | Morita et al. ............... 310/365 |
| 5,501,986 A | * | 3/1996 | Ward et al. .................. 436/525 |
| 5,548,178 A | * | 8/1996 | Eda et al. .................... 310/349 |
| 5,705,399 A | * | 1/1998 | Larue ......................... 436/501 |
| 5,734,098 A | | 3/1998 | Kraus et al. |
| 5,852,229 A | * | 12/1998 | Josse et al. ................. 73/24.06 |
| 5,929,555 A | | 7/1999 | Sugimoto et al. |
| 6,156,578 A | | 12/2000 | Tom |
| 6,500,547 B1 | | 12/2002 | Potyrailo |
| 6,513,361 B2 | * | 2/2003 | Miyake et al. ............. 73/24.06 |
| 7,098,574 B2 | * | 8/2006 | Iwata ......................... 310/320 |
| 7,183,698 B1 | * | 2/2007 | Chou et al. ................. 310/359 |
| 7,235,913 B2 | * | 6/2007 | Iwata ......................... 310/320 |
| 2006/0107733 A1 | * | 5/2006 | Aastrup et al. ............. 73/64.53 |
| 2006/0272396 A1 | * | 12/2006 | Itoh et al. ................... 73/64.53 |

OTHER PUBLICATIONS

Uttenthaler, E., Schraml, M., Mandel, J., and Drost, S. Ultrasensitive quartz crystal microbalance sensors for detection of M13-Phages in liquids. Biosensors & Bioelectronics, 16, 765-746 (2001).

Yamanaka, T., Yoshikawa, K., and T. Nakamoto. Improvement of odor-recorder capability of recording dynamical change in odor, Sensors and Actuators B: Chemical, 99 (2004) 367-372.

L. Zuxuan, M.D. Ward, C. M. Yip, I.S, Joseph. Operation of an Ultrasensitive 30 MHz Quartz Microbalance in liquids, Anal. Chem., 65 (1993) 1546-1551, 1.

G. Sauerbrey. The use of quartz oscillators for weighing thin films and for microweighing, Zeitschrift fur Physik, (1959) 206-222.

E. Uttenthaler, M. Schraml, J. Mandel, S. Drost. Ultrasensitive quartz crystal microbalance sensors for for detection of M13-phages in liquids, Biosensors and Bioelectronics, 16, (2001) 735-743.

D.A. Neumeier. Chemical milling of quartz using a solution based on organic solvents and anhydrous hydrofluoric acid, 2002 IEEE International Frequency Control Symposium and PDA Exhibition (2002) 394-402.

R.W. Ward. Etching of Quartz Crystal Spheres, Salt Lake City, Utah, 1993 IEEE International Frequency Control Symposium (1993) 390-396.

R.S. Barratt. The preparation of standard gas mixtures, A Review, The Analyst, 106 (1981) 817-849.

J.W. Grate. S.N. Kaganova, V.R. Bhethanabotla. Examination of mass and modulus contributions to thickness shear mode and surface acoustic wave vapor sensor responses using parition coefficients, Faraday Discussion, 107 (1997) 259-283.

J.W. Grate, A.W. McGill. Dewetting Effects on Polymer Coated Surface Acoustic Wave Vapor Sensors, Anal. Chem., 67 (1995) 4015-4019.

* cited by examiner

HIGH FREQUENCY THICKNESS SHEAR MODE ACOUSTIC WAVE SENSOR FOR GAS AND ORGANIC VAPOR DETECTION

CROSS REFERENCE TO RELATED APPLICATIONS

This application claims priority to currently pending U.S. Provisional Patent Application 60/703,371, entitled, "High Frequency Thickness Shear Mode Sensors for Gas and Organic Vapor Detection", filed Jul. 28, 2005, the contents of which are herein incorporated by reference.

FIELD OF INVENTION

This invention relates to quartz crystal microbalance systems. More specifically, this invention relates high frequency thickness shear mode sensors for gas and organic vapor detection.

BACKGROUND OF THE INVENTION

Sensing elements in polymer-coated vapor sensors are often surface acoustic wave (SAW) devices. To overcome selectivity limitations, arrays of SAW sensors are used, employing a micro-sensor system format which has pre-concentration, chromatographic column resolution and array detection stages [1]. One reason for this choice of SAW devices is the higher sensitivity afforded by these typically higher frequency devices. Thickness shear mode (TSM) devices, also called the quartz crystal microbalance (QCM), have been employed in many analytical applications, and as commercial thickness monitors in deposition equipment, however, their use in vapor and gas sensing is not common, although, some electronic nose type systems do employ them in odor sensing, which is essentially a vapor sensing application [2-5]. Some advantages of the TSM devices include simpler electronics, better baseline stability, less involved design and fabrication, and well-developed response models.

Most TSM applications so far have utilized devices in the 5-20 MHz fundamental resonance frequency range. Commercial resonators have been manufactured routinely for some time by thinning quartz plates by chemical milling to oscillate at fundamental frequencies of a little over 100 MHz and stable oscillators at fundamental and overtone frequencies are readily available. However, such higher frequency devices have rarely been tested in sensing applications and never in gas phase applications [6]. A concern in utilizing TSM devices of greater than about 20 MHz fundamental frequency in sensor applications is the fragility resulting from the thin piezoelectric material that is necessary for obtaining higher fundamental frequencies. To provide mechanical stability, devices are fabricated by surrounding a thin oscillating region with a thick outer ring. In addition to the fragility, such thin plates (of the order of 2 micron for a 100 MHz quartz device) could lead to baseline stability and consequent limit of detection issues. Finally, the active sensor area is typically reduced by design limitations on the ratio of the oscillating region to the outer ring, and the absolute value of the oscillating region, leading to sensor performance issues that cannot be predicted easily.

SUMMARY OF INVENTION

Thickness shear mode (TSM) quartz resonators at a fundamental frequency of 96 MHz were evaluated for their performance in organic vapor sensing applications and results were compared with the performance of 10 and 20 MHz resonators. These devices were produced by chemical milling of AT-cut quartz. Seven test organic vapors were utilized at concentrations ranging from 0.2 volume percent to 13.7 volume percent in the vapor phase. In all cases, the rubbery polymer poly(isobutylene) was used as a sensing layer. Detailed results for various sensor parameters such as sensitivity, baseline noise and drift, limit of detection, response and recovery times, dynamic range, and repeatability for the 96 MHz device were compared with those for 10 and 20 MHz devices. The test case of benzene/poly(isobutylene) was chosen to make these detailed comparisons, and the general conclusions were found to be similar with other solvents. As expected, the 96 MHz device was found to be more sensitive than the lower frequency devices. Device sensitivity was dependent on the benzene concentration. An enhancement factor of 8 to 27 when compared to the 10 MHz device was seen as the benzene concentration ranged from 0 to nearly 7 volume percent in the vapor phase. Significantly higher enhancements for the 96 MHz device were limited by difficulty in coating thicker sensing layers without damping out the response. No significant improvement in the limit of detection was found in going to higher frequencies due to increased baseline noise. Response and recovery times were smaller for the 96 MHz device. Response times decreased with analyte concentration. Sensor response was in reasonable agreement with the perturbation model of Sauerbrey at lower concentrations and deviated at the higher concentrations for the 96 MHz device. Higher frequency TSM devices can be very useful as organic vapor sensors both in detection and process monitoring applications. These devices have the advantages of simpler electronics, easier design and fabrication, well-developed models and good baseline stability when compared to other acoustic wave devices.

According to one aspect of the present invention there is provided a thickness shear mode (TSM) sensor. The TSM sensor includes a quartz crystal having an oscillating region of reduced thickness surrounded by a outer region, wherein the outer region is comparatively thicker than the oscillating region, an electrode and a polymer sensing film in contact with the oscillating region of the quartz crystal. By employing a thicker outer region mechanical stability is imparted upon the sensor while allowing the desired frequency in the oscillating region. In certain embodiments the polymer is a viscoelastic polymer. The polymer can polyvinyl acetate, polyvinyl pyrrolidone, polyisobutylene, polystyrene and polystyrenebutadiene. In an advantageous embodiment the polymer is polyisobutylene. In certain embodiments the frequency of the polymer coated resonator is greater than 20 MHz, 30 MHz, 40 MHz, 50 MHz, 60 MHz, 70 MHz, 80 MHz or 90 MHz. In other embodiments the frequency of the polymer coated resonator is about 96 MHz. In yet other embodiments the frequency of the polymer coated resonator is between 20 and 200 MHz, 50 and 150 MHz or 80 and 120 MHz. In still other embodiments the frequency of the polymer coated resonator is about 96 MHz and the polymer is polyisobutylene.

According to a second aspect of the present invention there is provided a method of gas or vapor sensing in an analyte. The method includes the steps of (1) providing a thickness shear mode (TSM) sensor (2) contacting the TSM sensor with the analyte and (3) measuring the frequency shift of the sensor upon contact with the analyte. The frequency shift is indicative of the presence or concentration in the analyte of the gas or vapor to be sensed. The provided TSM sensor includes a quartz crystal having an oscillating region of reduced thickness surrounded by a outer region, an electrode; and a polymer sensing film in contact with the oscillating region of the quartz crystal. The outer region of the quartz crystal is comparatively thicker than the oscillating region. In certain embodiments the gas or vapor is an organic gas or vapor. The gas or vapor can be benzene, hexane, cyclohexane, heptane, dichloroethane, chloroform, and toluene. In an advantageous embodiment the gas or vapor is benzene. In certain embodiments the polymer is a viscoelastic polymer. The polymer can be polyvinyl acetate, polyvinyl pyrrolidone, polyisobutylene, polystyrene and polystyrenebutadiene. In an advantageous embodiment the polymer is polyisobutylene. In certain embodiments the frequency of the polymer coated resonator is greater than 20 MHz, 30 MHz, 40 MHz, 50 MHz, 60 MHz, 70 MHz, 80 MHz or 90 MHz. In other embodiments the frequency of the polymer coated resonator is about 96 MHz. In yet other embodiments the frequency of the polymer coated resonator is between 20 and 200 MHz, 50 and 150 MHz or 80 and 120 MHz. In still other embodiments the frequency of the polymer coated resonator is about 96 MHz and the polymer is polyisobutylene.

According to a third aspect of the present invention there is provided a method of fabricating a sensor to detect organic gas or vapor. The method includes the steps of the steps of (1) providing an AT-cut quartz crystal, (2) milling the oscillating region of the crystal and coating the AT-cut crystal with a chemically-sorbent polymer. The coated oscillating region of the crystal has a frequency greater than about 20 MHz. In certain aspect of the invention the chemically-sorbent polymer is a viscoelastic polymer. The polymer can be polyvinyl acetate, polyvinyl pyrrolidone, polyisobutylene, polystyrene and polystyrenebutadiene. In an advantageous embodiment the polymer is polyisobutylene. In certain embodiments the frequency of the polymer coated resonator is greater than 20 MHz, 30 MHz, 40 MHz, 50 MHz, 60 MHz, 70 MHz, 80 MHz or 90 MHz. In other embodiments the frequency of the polymer coated resonator is about 96 MHz. In yet other embodiments the frequency of the polymer coated resonator is between 20 and 200 MHz, 50 and 150 MHz or 80 and 120 MHz. In still other embodiments the frequency of the polymer coated resonator is about 96 MHz and the polymer is polyisobutylene. In certain embodiments the AT-cut quartz crystals include electrodes on opposing surfaces of the oscillating region of the crystal. The electrodes can be circular electrodes fabricated in gold.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
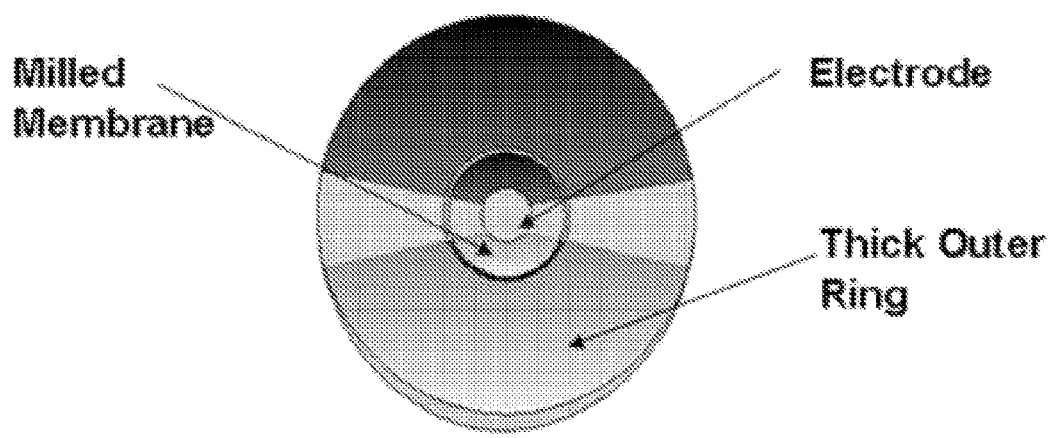
FIG. 1 is an illustration of a milled TSM device according to the present invention.

The present invention provides a higher frequency device with polymeric sensing layers useful in organic vapor and gas sensing applications. Typical sensor parameters of sensitivity, dynamic range, response and recovery times, baseline stability, frequency noise, limit of detection, and robustness were explored using an exemplary 96 MHz fundamental mode resonant frequency device. This device was compared to 10 and 20 MHz frequency devices. Higher frequency devices such as these provide an alternative technology in gas detection applications, as well as provide viable process concentration sensors for on-line monitoring. Devices of these different frequencies were of different sizes, to meet design parameters of mechanical strength, mounting, and other considerations.

1. INTRODUCTION

To construct gas or vapor sensors, chemically-sorbent films are commonly coated onto TSM resonators. Chemical sensitivity and selectivity is imparted by attaching a thin film to the acoustically active region of the TSM device. Devices employed in this work were AT-cut quartz crystals with circular gold electrodes on both sides. Because of the piezoelectric properties of the quartz material, application of a voltage between the two electrodes at the surface results in a shear deformation of the crystal. The quartz crystal then vibrates via the piezoelectric effect and this vibrational motion results in the generation of a transverse acoustic wave that propagates across the thickness of the quartz crystal. The resonant frequency of the TSM device decreases with the crystal thickness when a standing wave condition is met, as $$t_q = \frac{\lambda_q}{2} \qquad (1)$$

$$v = \left(\frac{\mu_q}{\rho_q}\right)^{1/2} \qquad (2)$$

Here v is the velocity of sound in the quartz and $t_q$ is the quartz thickness. Equation 2 gives the velocity, where $\rho_q$ is the density (2.648 g cm$^{-3}$) and $\mu_q$ is the shear modulus (2.947× 10$^{11}$ g cm$^{-1}$ S$^{-2}$) of the quartz. Since the quartz thickness is much larger than the electrode thickness, the electrodes are neglected when determining the resonant frequency. Equations have been developed to yield expressions for the dependence of the resonant frequency on the mass changes occurring within films coated onto the TSM sensor. The Sauerbrey equation is one such relationship, valid for small mass loadings, such as those occurring in vapor sensing applications:

$$\Delta f = \frac{2f_r^2 \Delta m}{(\mu_q \rho_q)^{1/2}} \quad (3)$$

where $\Delta f$ is the measured frequency shift, $f_r$ is the resonant frequency, and $\Delta f$ is the film areal mass density (which can be related to the film mass) [7]. Changes in the film mass will cause frequency shifts; these frequency shifts are dependent upon the film selectivity and the device sensitivity. In Sauerbrey's model, the sensitivity $c_f$ is given by:

$$c_f = \frac{2f_r^2}{\rho_q v_q} \quad (4)$$

Consequently, a commonly used 10 MHz AT-cut quartz crystal (with the previously mentioned physical properties) will have a mass sensitivity of $2.26 \times 10^8$ Hz cm$^2$ g$^{-1}$. The addition of material with an areal density of 4.42 ng cm$^{-2}$ will cause a 1 Hz shift in this resonator, which is easily measurable using common electronics.

Although a 10 MHz TSM sensor already has a high degree of theoretical sensitivity, it is obvious from equation (4) that this sensitivity can be considerably increased by increasing the resonant frequency. For a 56 MHz device, experimental sensitivity increases proportional to the 2.88 exponent of the resonant frequency have been reported for liquid sensing with the signal to noise ratio improving by a factor of 6.5[8]. This 2.88 power dependence is greater than predicted by Sauerbrey's model, which is not applicable for liquid phase operation. Even with sensitivity increases predicted by the Sauerbrey model, which is more likely valid for gas phase operation, a 100 MHz device will be 100 times more sensitive than a 10 MHz device, and twice as sensitive as a 100 MHz Rayleighwave SAW device fabricated in quartz and responding via the mass loading effect [9]. Achieving higher frequencies requires thinner quartz crystals. This is difficult to accomplish using conventional fabrication techniques. However, higher frequency devices can be produced by operating at overtones of the fundamental resonant frequency or by using milled devices [10].

The plate thickness $t_q$ determines the wavelength of the fundamental (n=1) and harmonic (n=3, 5, 7 . . . ) resonances as $$f_n = \frac{nv}{2t_q} \quad (5)$$

where $f_n$ is the frequency of the $n^{th}$ harmonic. Milled crystals are made thinner only in the center so that a thin quartz membrane is fabricated with a thick outer ring allowing for mechanical stability. The design of high frequency resonators by milling techniques has been studied extensively [11-14]. These higher frequency devices are long known to have improved mechanical stability and frequency-to-noise ratios at are better than other acoustic wave devices [15]. Chemically milled devices specifically designed for the experiments below experiments, with fundamental frequencies of approximately 96 MHz having approximately 20 mils electrode diameter were fabricated at MTronPTI, Orlando, Fla. A diagram of a milled TSM device is shown in FIG. 1.

Example

High Frequency TSM Sensor 2.1 Apparatus Set-up

Figure 2:
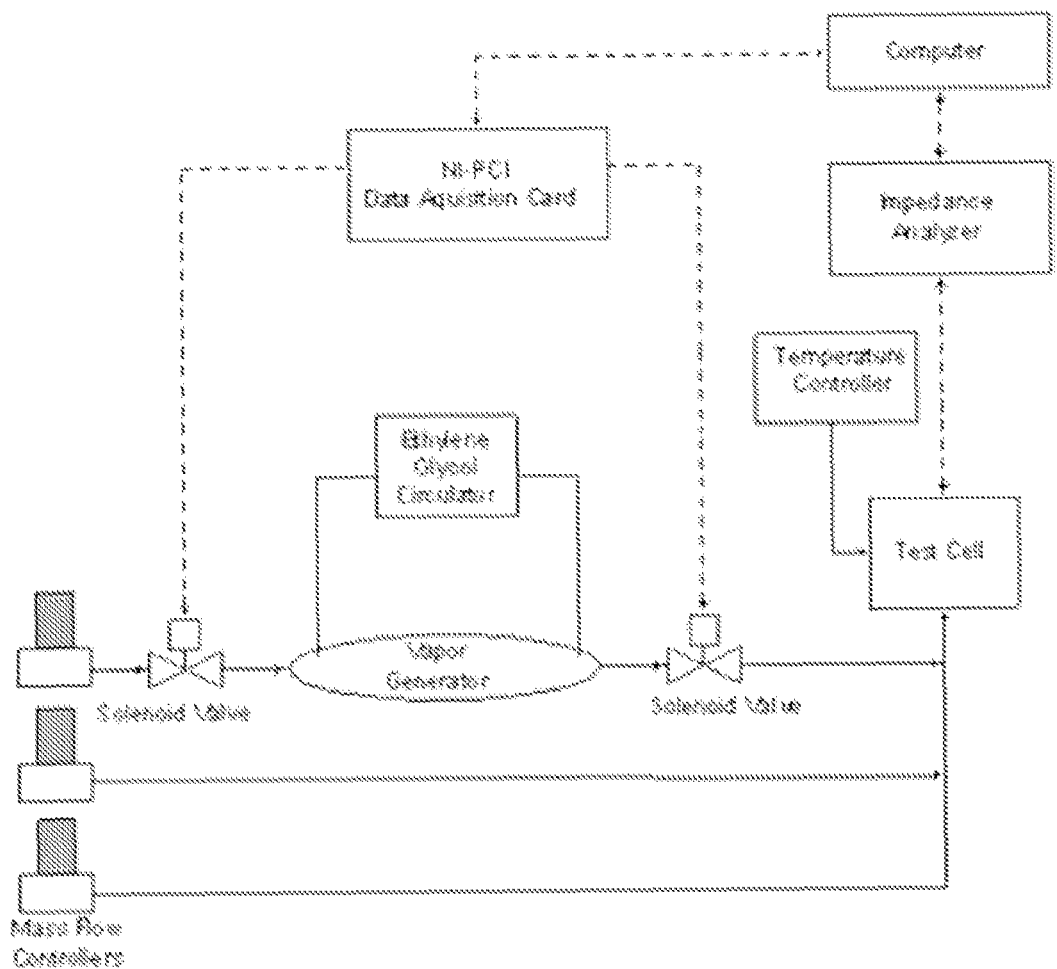
FIG. 2 is a schematic of a vapor generating apparatus.

Organic vapor samples were generated at specific concentrations to test the coated TSM sensors. Among the available techniques for generating standard gases, a dynamic method of generating vapor samples was used [16-18]. The equipment is fully automated and a schematic diagram is shown in FIG. 2.

Organic liquids were contained in four bubbler units housed in a temperature bath. MKS mass flow controllers were used to regulate nitrogen carrier gas through the bubbler units. Each bubbler unit consisted of a flask in which the organic liquid was contained. Multiple mass flow controllers (100 sccm, and 200 sccm) allowed for variation of test sample concentrations. Three streams were used: The carrier stream passing through the bubbler, and the diluting streams. The vapor pressure of the liquid at the bubbler temperature was calculated using an accurate vapor pressure correlation (Wagner's equation) [19]. The mole fraction was approximated from the volume of the vapor generated, assuming saturation of the exiting vapor from the bubblers. The generated vapor was further diluted and a new diluted mole fraction was calculated. This mole fraction was equated to the volume fraction and then the concentration was approximated using the ideal gas law. Activities of the solvents in PIB, calculated using these experimental data, matched very well with literature values, indicating that the vapor concentrations were being generated accurately [20]. Further calibration of the dilution system using charcoal traps and weighing also indicated that the vapor generation system functioned as designed. Generated vapor concentrations were estimated to be well within 10% of true values. An Agilent 4294A precision impedance analyzer was used to monitor the resonant frequency and equivalent circuit parameters of the TSM devices. A custom-made stainless steel test cell was designed for housing the sensor and was kept under temperature control. The TSM device was attached to a printed circuit board using a commercially available socket holder, obtained from International Crystal Manufacturing, Oklahoma City, Okla., for 10 MHz and 20 MHz resonators and a transistor socket for the higher fundamental frequency resonators (96 MHz). The sockets facilitated easy removal of the sensors without disturbing electrical connections.

2.2 Coating and Chemicals

TSM devices were coated by spray coating utilizing an air brush [21]. Poly(isobutylene) (Acros) was used as the sensing film. The polymer had an average molecular weight of 400,000. A dilute solution of the polymer (0.1%), dissolved in chloroform (99.9% HPLC), was aspirated through an atomizing nozzle using compressed nitrogen gas. As the atomized droplets impact the device surface, the volatile solvent is evaporated with a heat gun to leave the polymer coating. Polymer coatings formed using this method may have irregular texture and coverage. However, thicknesses were reproducible because the device frequency was monitored throughout the coating process. The resonators were soaked in chloroform and cleaned in a Harrick plasma cleaner prior to coating. The polymer was coated to equal thickness on each side of the TSM resonators to achieve various frequency shifts corresponding to different film thicknesses. The devices were allowed to air dry after each coating application, and were cured to anneal the film. Unless handled with care, the 96 MHz frequency resonators were found to be fragile and shattered during spray coating. Upon refining the coating process, devices were handled without damage through several cycles of coating, experimentation and cleaning. The frequency and equivalent circuit parameters of the uncoated device were recorded before and after application of the polymer. These parameters of the device were also monitored with time throughout sorption and desorption of the vapors in the polymer.

A TSM device is only a resonator if there is no sensing film. The sensing film imparts selectivity and sensitivity towards a particular chemical, thus, making a resonator into a sensor. The sensing films used were polymer coatings. The coating should physically or chemically bond to the surface of the TSM resonator and should behave as an ideal mass layer. An ideal mass layer should be infinitesimally thick when compared to the thickness of the quartz material (ignoring the thickness of the gold electrodes). The polymer coatings were applied to both sides of the electrodes, but the total film thickness was calculated as the sum of thickness on both sides of the resonator. In effect the actual film thickness is the half of the total film thickness. Since different resonators were compared in this study, the physical characteristics of the resonators were different, with each sensor having a different electrode area. Since only the coated electrode area is region of the sensor surface where the coating analyte interaction (physisorbtion) occurs, comparing the sensitivity of devices with different electrode areas is inaccurate. The model developed equation (11) accounts for these differences, however, the polymer film coating $\Delta f_p$, must be similar for all devices. Since each device has a different sensitivity, the frequency shift due to the polymer coating will be different, but the thickness can be constant. Another complication to having similar film thickness, however, is introduced because each device has a different quartz blank thickness. Consequently, the ratio of the thickness of the quartz blank to the polymer film must be kept constant. This ratio was approximately 0.5%. The uniformity of the film has little effect on the detection of the chemical vapors, however the film should be adherent and stable in the presence of the organic vapors. Several methods are available for coating TSM resonators including spin coating, spray coating, drop coating and coating using an oscillating capillary nebulizer. The performance of several polymer film coatings of poly-vinyl acetate, poly-vinyl pyrrolidone, polystyrene-butadiene, and poly-isobutylene were. The results based on several performance criterion were used to select the appropriate film. Since, we were sensing for organic vapors, rubbery polymer films known to physisorb with organic vapor, such as the ones mentioned previously, were selected. Nevertheless, some films perform better for a given application and polymer properties, such as glass transition temperatures, which should be taken into account when choosing the sensing film.

2.3 The TSM Devices

Figure 3:
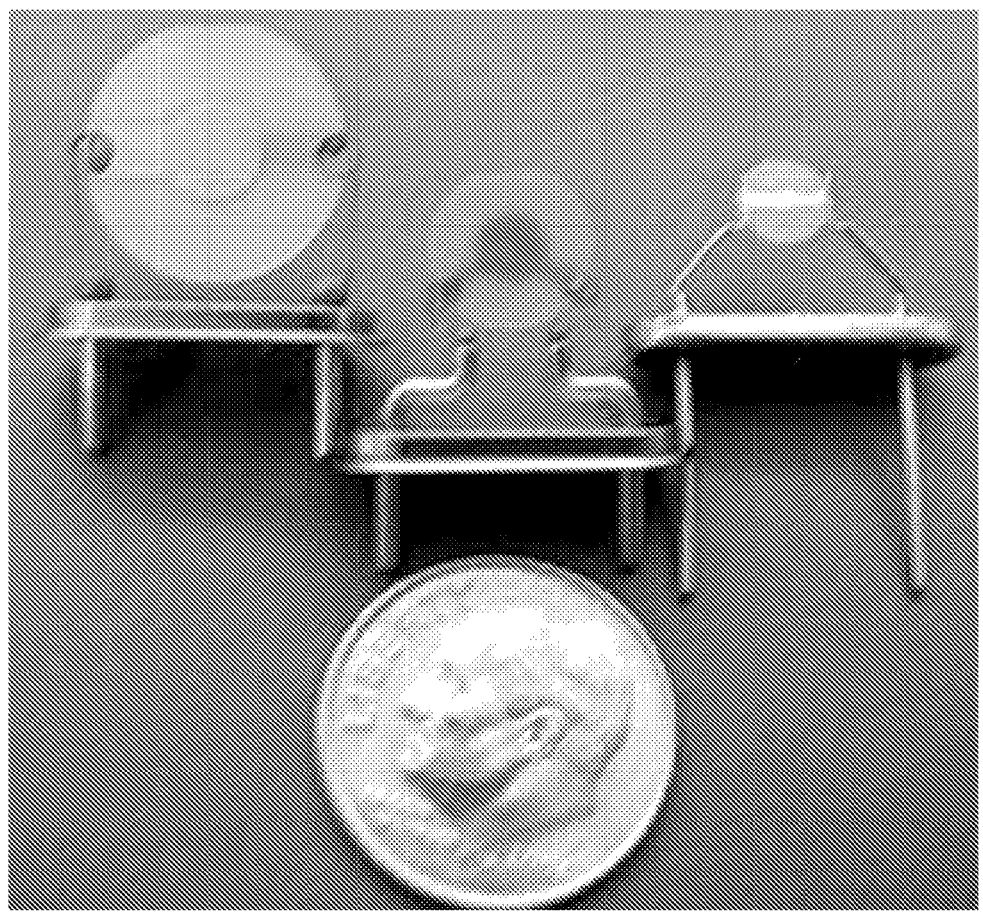
FIG. 3 is a photograph of 10 (left), 20 (middle), and 96 (right) MHz TSM devices.

All crystals were AT-cut quartz with gold electrodes on a chromium adhesion layer. Some parameters of the devices are given in Table 1. The milled membrane diameter of the 96 MHz device was approximately 0.127 cm. The 10 and 20 MHz devices were obtained from International Crystal Manufacturing. The 96 MHz devices were specially fabricated at MTronPTI, Orlando, Fla., using chemical milling. The resonator quartz blanks were etched in $NaOH.0.5H_2O$ at 180° C. Additionally, these resonators were fabricated with ring thicknesses of approximately 50 μm and membrane thicknesses of approximately 17 μm. FIG. 3 is a photograph of the mounted, chemically milled 96 MHz resonator, along with the 10 and 20 MHz devices used for comparison.

TABLE 1

Parameters of the TSM devices

| Resonator (MHz) | Blank Diameter (cm) | Electrode Diameter (cm) | Electrode Thickness (Å) | Electrode Material | Milled Area (cm$^2$) |
|---|---|---|---|---|---|
| 9.98 | 1.376 | 0.5105 | 1000/100 | Au/Cr | — |
| 19.97 | 0.8077 | 0.3480 | 1000 | Au/Cr | — |
| 96.89 | 0.508 | 0.0508 | — | Au/Cr | 0.0507 |

3. PERFORMANCE TESTING OF FABRICATED DEVICES

Performance of the TSM device with a poly(isobutylene) sensing film tested with benzene analyte is presented below. This typical case of an organic solvent and a rubbery polymer is chosen to evaluate the dependence of sensor parameters on frequency. Each of the resonators in Table 1 was exposed to various concentrations of benzene. The frequency responses of the sensors were recorded during exposure to compare the sensitivities, frequency noise, limits of detection, response and recovery times, and dynamic range for the three devices.

The vapor phase concentration was increased from 27,557 mg/m$^3$ to 232,688 mg/m$^3$, with purges of pure nitrogen gas between each exposure to allow the benzene vapor to desorb and the film to recover. A total flow rate of 100±1 sccm was always maintained over the surface of the device. The temperature of the cell was maintained at 22.5° C. and the benzene vapor was generated at 15° C. Temperature fluctuations of the cell were within ±0.1° C. Frequency measurements taken using Labview and the Agilent impedance analyzer were stable to within ±1 Hz.

Film thickness of the coated polymer and associated frequency shift for each resonator is given in Table 2. The ratio of the polymer film to the quartz membrane thickness is kept below 1% to stay within the mass balance regime within which Sauerbrey's equation is known to be valid for inertially coupled layers. Also, sensor response dampens as the polymer film thickness is increased, such that a limit of sensing film thickness exists for each sensor of a given fundamental resonant frequency. Since different resonators have different blank thicknesses, the thickness of the polymer sensing film cannot be constant. However, the ratio of the thickness of the quartz blank to the thickness of the film can be kept at a near constant ratio to facilitate more rational comparison of sensor response parameters. Due to the higher sensitivity of the 96 MHz device, this constancy was difficult to achieve, leading to a slightly higher value, but still within 1%. In the experiments conducted, the responses of each resonator to various concentrations of benzene were recorded. From these data various sensor response parameters were determined and compared.

TABLE 2

Polymer film parameters

| Resonator Frequency (MHz) | Film Thickness (nm) | Frequency Shift (kHz) | Thickness Ratio (percent) |
|---|---|---|---|
| 9.993250 | 961 | 20,112 | 0.58 |
| 19.993400 | 420 | 34,440 | 0.50 |
| 96.999522 | 141 | 275,413 | 0.82 |

3.1 Sensor Response, Repeatability, and Dynamic Range

Figure 4A:
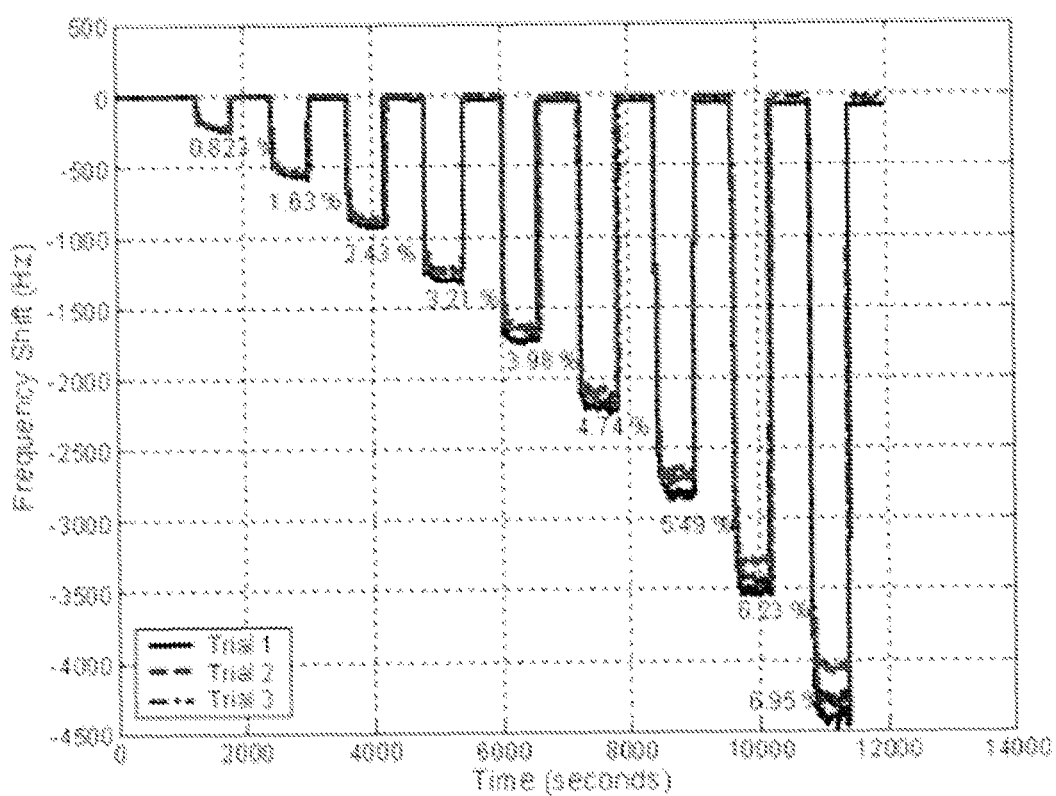
FIG. 4 is a graph illustrating repeatable sensor responses for the (A) 10, (B) 20 and (C) 96 MHz devices.
Figure 4B:
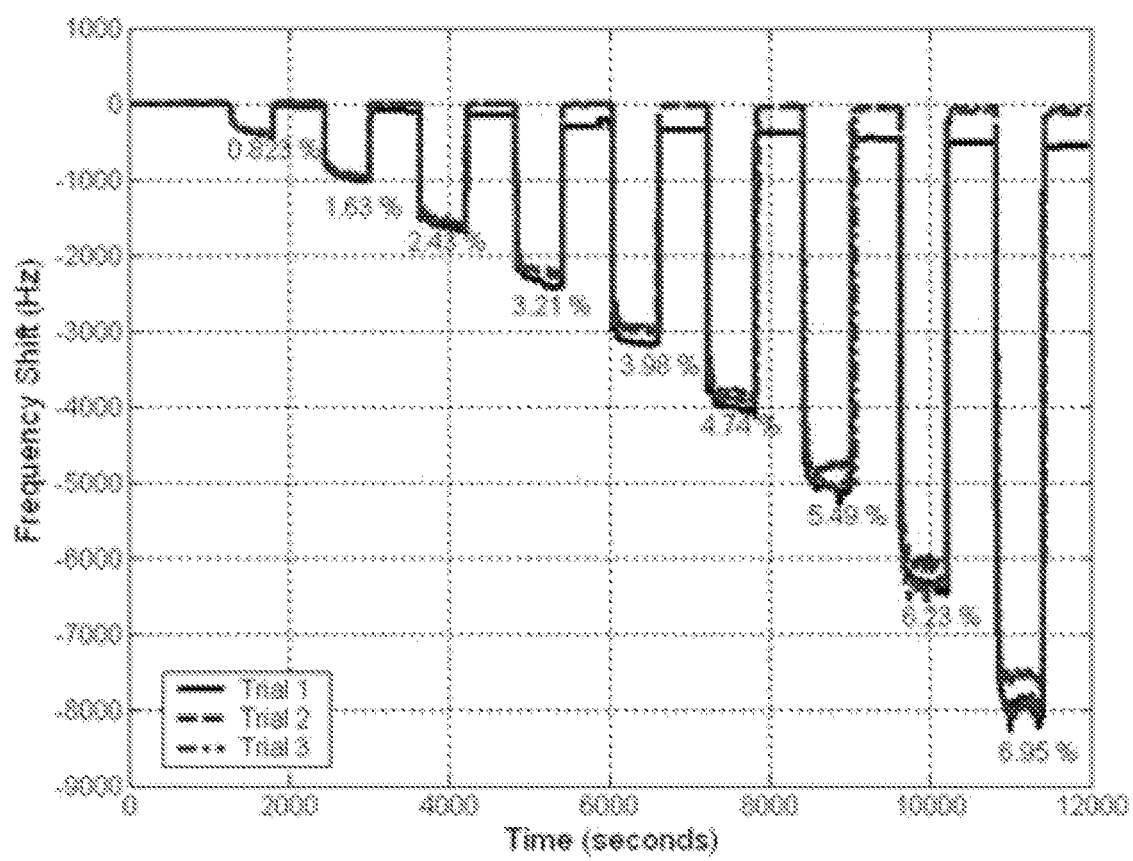
Figure 4C:
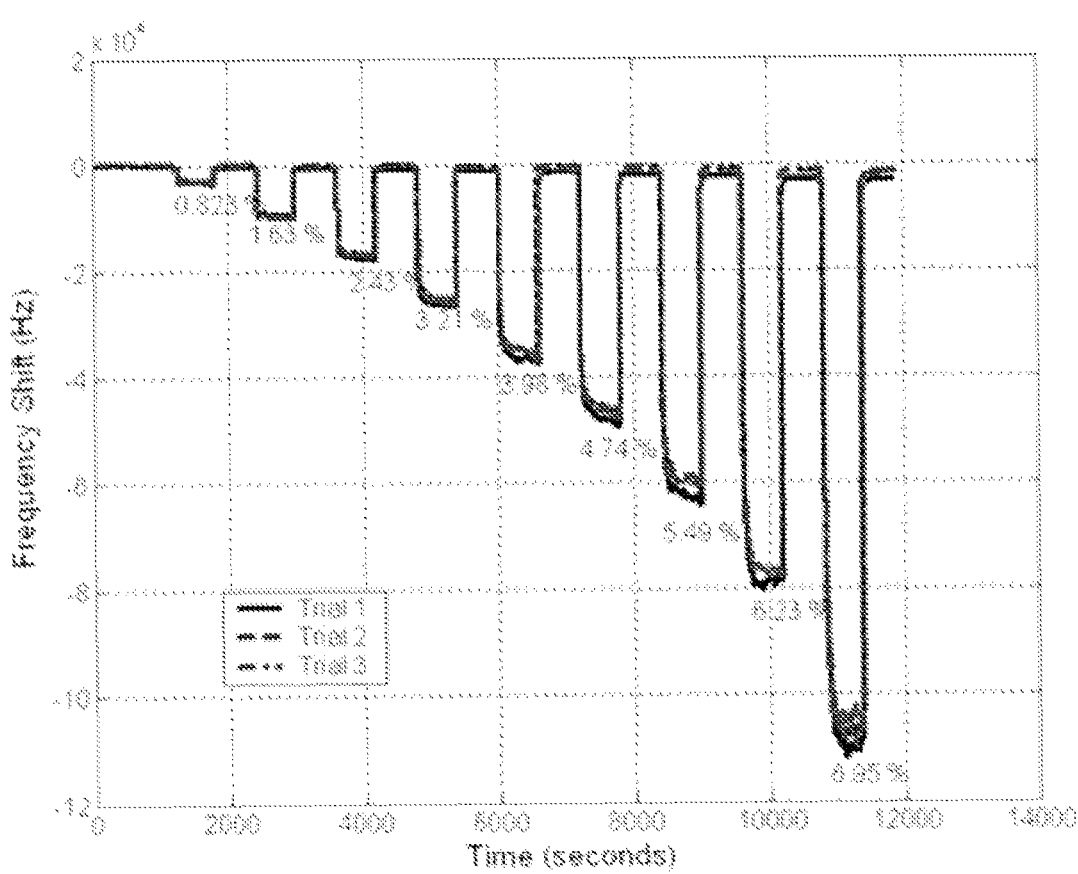
Figure 5:
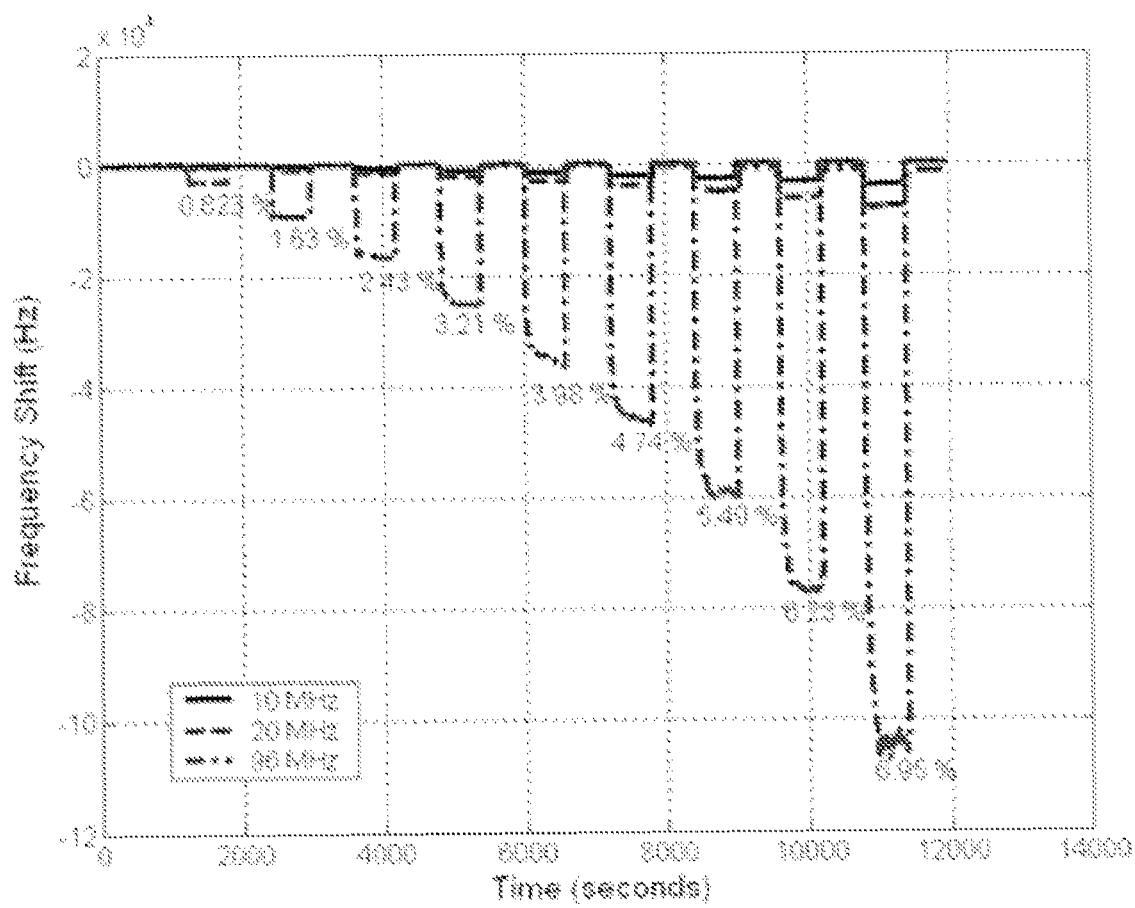
FIG. 5 is a graph illustrating a comparison of TSM sensor responses.

The resonator responses (frequency changes) due to exposure to the analyte are repeatable as shown in FIG. 4. Three trials were conducted with each device. Each run consisted of 1200 seconds of an initial purge with ultra high purity nitrogen, after which exposure and purge times were of 600 seconds duration each. The procedure was chosen to demonstrate the viability of the resonator as a sensor in terms of recovery after exposure to the test sample. Repeated cycling and re-testing of the polymer coated devices after several weeks yielded the same results. The inherent increase in sensitivity of the 96 MHz resonator, due to the increase in resonant frequency, is demonstrated by a comparison of the sensor response from each resonator, as shown in FIG. 5.

A noticeable drift in the baseline frequency was observed for all resonators. The base line drift for the 10 MHz device over the duration of the entire experiment of 12,000 seconds was 49 Hz. The 20 MHz and 96 MHz resonators had higher baseline drifts of 260 Hz and 2342 Hz, respectively. The baseline drift was probably the result of dewetting effects. De-wetting affects the shape of a thin film polymer by reducing the area of the film/surface interface. During exposure to the analyte the polymer film likely breaks up into beads of isolated droplets. This effect was also observed during the coating procedure and has also been noted in previous studies [22]. The frequency of the polymer coated resonators was observed to increase slightly when left overnight. This was probably due to absorption of water vapor from the air. Consequently, the initial rise in resonant frequency during first exposure to pure nitrogen is due to de-sorption of the water.

Table 3 shows the dynamic range of seven organic vapors (benzene, hexane, cyclohexane, heptane, dichloroethane, chloroform, and toluene) which were tested with these poly (isobutylene) coated resonators. These ranges are useful in considering the TSM devices as process stream concentration monitors. All these organic solvents are reasonably soluble in the rubbery polymer poly(isobutylene), although frequency shifts at exposures of same concentrations are different for different organics, allowing for possibility of discrimination. However, the focus of this study is to evaluate the higher frequency 96 MHz device for possible improvements over the lower frequency devices in a comparative study of the three devices. Benzene analyte sensor response parameters are presented as a typical case. Sensor response parameters for the other organics from Table 3 led to similar conclusions.

TABLE 3

Dynamic range of TSM devices for several organic vapors

| Chemical | Dynamic Range (Volume percent) | | |
|---|---|---|---|
| | 10 MHz | 20 MHz | 96 MHz |
| Benzene | 0.8-7.0 | 0.8-7.7 | 0.8-7.0 |
| Toluene | 0.2-1.3 | 0.2-1.5 | 0.2-1.5 |
| Hexane | 1.4-9.2 | 1.4-11.5 | 1.4-9.2 |
| Heptane | 0.4-2.5 | 0.4-3.2 | 0.4-2.9 |
| Cyclohexane | 0.9-6.5 | 0.9-8.0 | 0.9-6.5 |
| Dichloroethane | 0.7-5.8 | 0.7-6.4 | 0.7-6.4 |
| Chloroform | 2.0-13.7 | 2.0-15.2 | 2.0-13.7 |

3.2 Sensitivity

Sauerbrey's model (equation 3) can be utilized to calculate the theoretically expected sensitivity for this polymer sorption process for each of the tested devices, provided the conditions for its validity are met, viz, the polymer/solvent adlayer should behave as a rigid, inertial mass perturbation to the quartz thickness. This model provides an expression for frequency sensitivity to areal mass density (mass/unit active area of crystal), however, the active area is not known exactly. Hence, comparison with theory becomes convenient if an experimental sensitivity to areal mass density were expressed in terms of easily measured parameters. To establish if each of the three devices tested behaves according to Sauerbrey's model, we derive an expression for the experimental sensitivity in the following way:

The frequency shift due to the polymer and sorbed solvent in the sensing film for each exposure is:

$$\Delta f = \Delta f_p + \Delta f_s \quad (6)$$

where $\Delta f_p$ is the frequency shift due to the polymer and $\Delta f_s$ is the frequency shift due to the solvent (analyte). Similarly, the areal mass density (mass/unit area) of the polymer/solvent sensing layer is given by:

$$\Delta m = \Delta m_p + \Delta m_s \quad (7)$$

We can define weight fraction of solvent in the polymer, w, in terms of the areal mass densities as:

$$w_o = \frac{\Delta m_s}{\Delta m_p + \Delta m_o} \quad (8)$$

Rearranging for $\Delta m_s + \Delta m_p$ $$\Delta m_s + \Delta m_p = \Delta m_p \left( \frac{1}{1 - w_s} \right) \quad (9)$$

Noting that the polymer film areal mass density equals hp, the product of the film thickness and polymer density, we have $$\Delta m_p + \Delta m_s = h\rho_p \left( \frac{1}{1 - w_s} \right) \quad (10)$$

The sensitivity becomes $$c_p = \frac{\Delta f_p + \Delta f_s}{h\rho_p \left( \frac{1}{1 - w_s} \right)} \quad (11)$$

This expression can be utilized for calculating experimental mass sensitivity as it involves no determination of actual mass loaded on the crystal, which is difficult to determine given that the active areas of the devices at different frequencies are both difficult to establish and are numerically different (due to different fabricated sizes). Since the mass involved is very small, there is no other easy technique available to weigh this loaded mass, necessary for establishing experimental sensitivity. However, equation 11 involves solvent weight fraction, which can be easily established from measurements taken with the 10 MHz device, provided this device behaves as a mass balance. This same weight fraction is applicable to the 20 and 96 MHz devices, for exposures at same vapor phase concentrations, if we assume that thermodynamic equilibrium is achieved between the polymer film and the vapor phase. In the experiments, the mass balance regime of the 10 MHz device was established by measurements of the equivalent circuit parameters, where the resistance values were reasonably constant for exposures at various concentrations tested. Thermodynamic equilibrium was confirmed by comparison of the measured solvent weight fractions to those from other literature thermodynamic measurements which utilized totally different sorption techniques [20]. The weight fractions were determined from frequency shifts by application of Sauerbrey's model to this 10 MHz device via $$w_s = \frac{\Delta m_s}{\Delta m_p + \Delta m_s} = \frac{\Delta f_s}{\Delta f_p + \Delta f_s} \quad (12)$$

Finally, the polymer thickness h was determined by profilometer measurements, as well as from measured frequency shifts $\Delta f_p$ and application of Sauerbrey's model for each device, before exposures to solvents. Poly(isobutylene) density was taken as 0.92 gm/cm$^3$, as given by the supplier Acros.

Figure 6A:
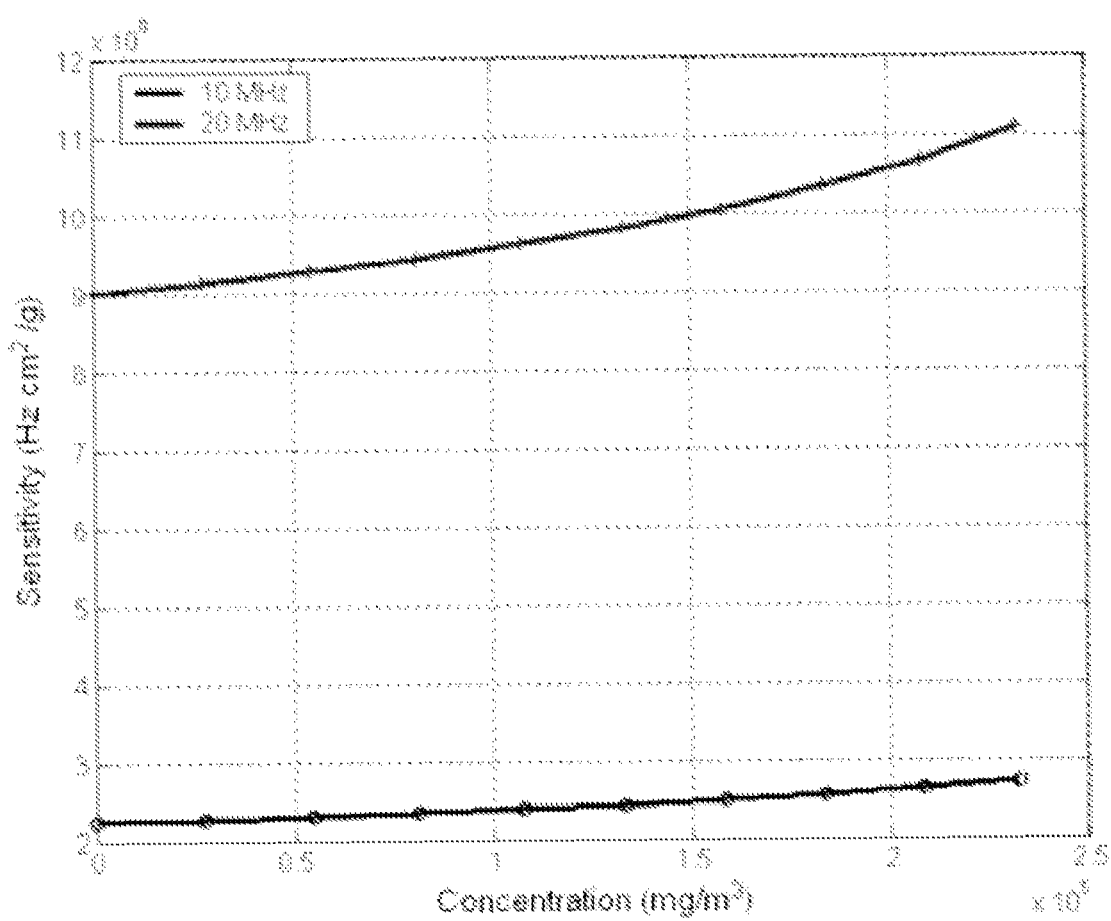
FIG. 6 is a graph illustrating the experimental mass sensitivities as functions of vapor concentration for the three devices (A) 10 and 20 MHz devices (B) 96 MHz device.
Figure 6B:
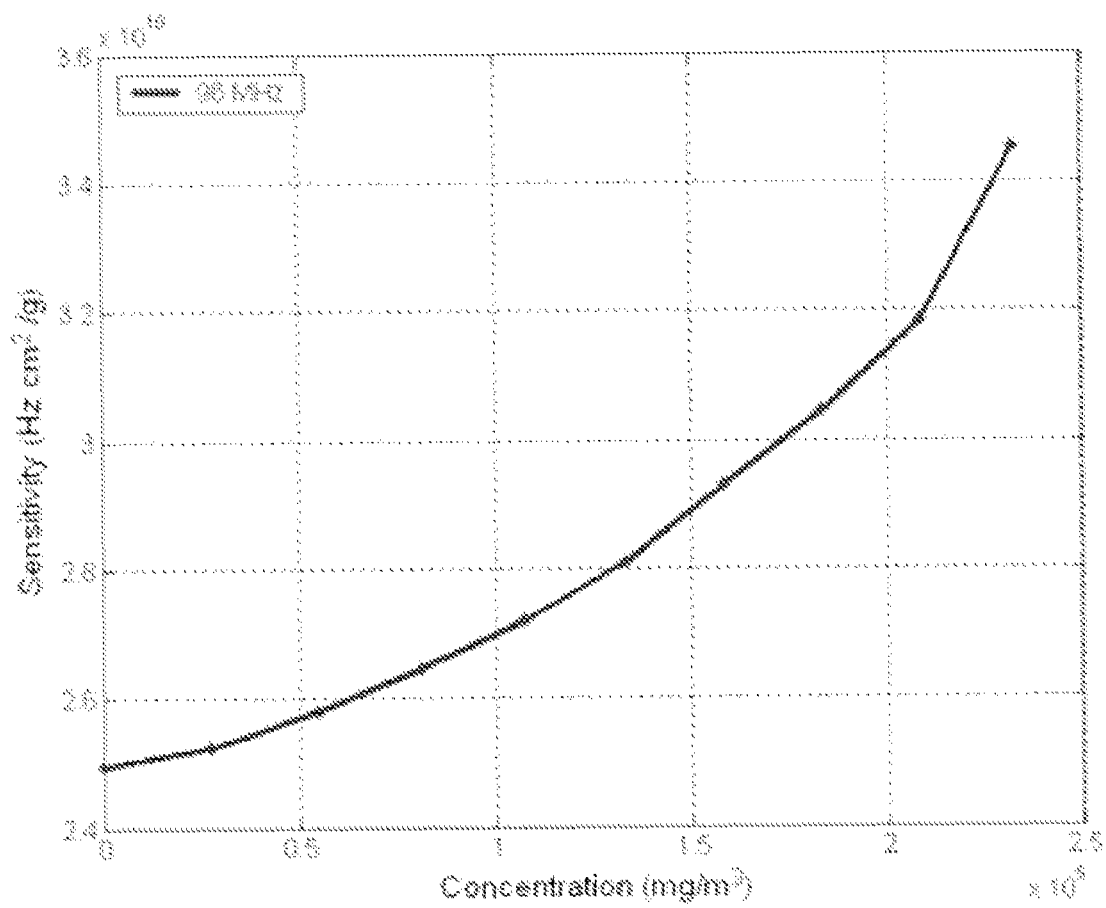

Experimental sensitivities for the devices at the three frequencies are shown in FIG. 6. These sensitivities are seen to be concentration dependent, more so for the 96 MHz device. The much larger sensitivity of this device in comparison to the lower frequency devices is shown in FIG. 6. Sauerbrey's model predicts 4-fold and 92-fold increases in areal sensitivity for the 20 and 96 MHz devices, respectively, in comparison to the 10 MHz device. The ratios range from 4.01 to 4.05, and 111 to 126, for the 20 and 96 MHz devices, respectively (FIG. 6). From linear regression at each vapor exposure concentration, we can establish whether the f$^2$ dependence predicted by Sauerbrey's model is borne out. We find that the exponent is close to 2, varying between 2.08 to 2.14, in going from the lowest to the highest exposure concentrations of benzene vapor. Note that the highest exposure concentration represents about 7 volume % benzene in the vapor phase, which corresponds to 17 weight % benzene in the polymer film. At the lower concentrations, the Sauerbrey model is followed well for all three devices. However, at the higher concentrations, with increased weight fractions of benzene in the polymer, the higher frequency device deviates to some extent from the model.

Figure 7A:
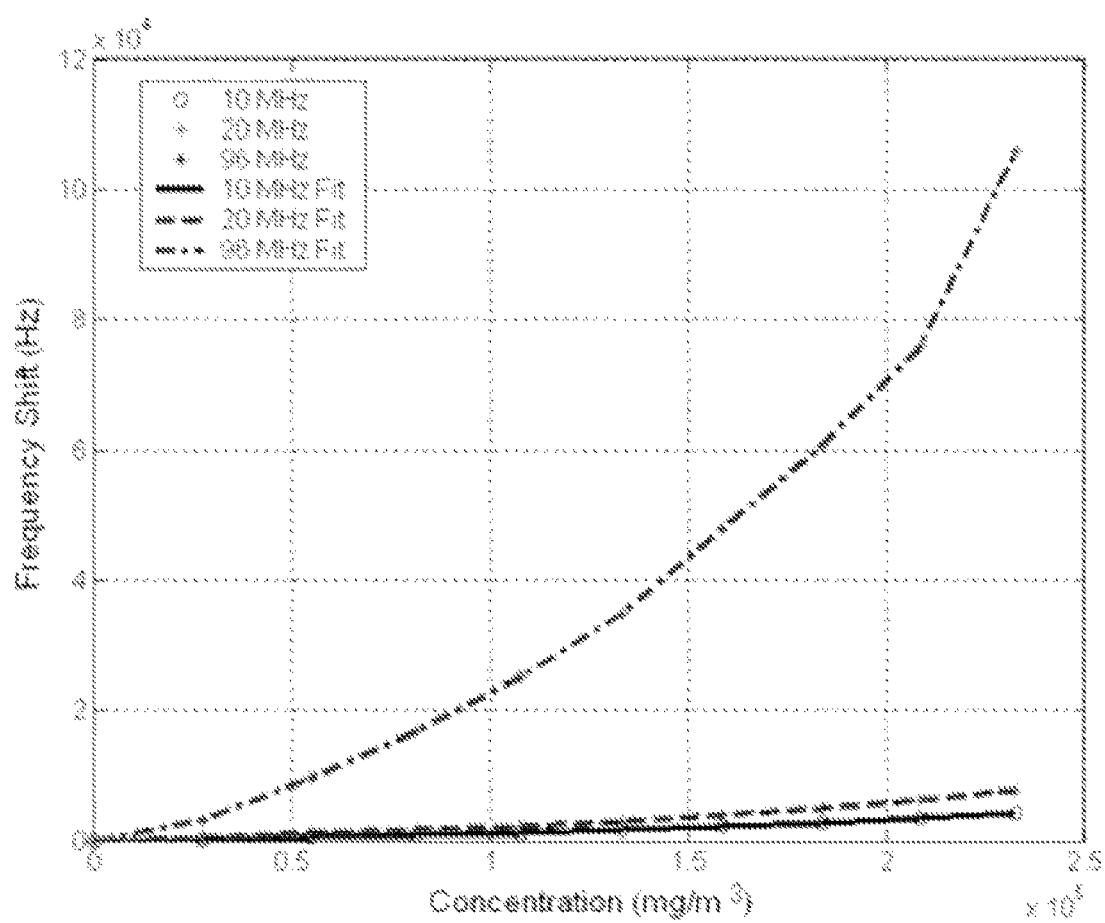
FIG. 7 is a graph illustrating the (A) calibration and (B) sensitivity of the three sensors as functions of vapor phase concentration.
Figure 7B:
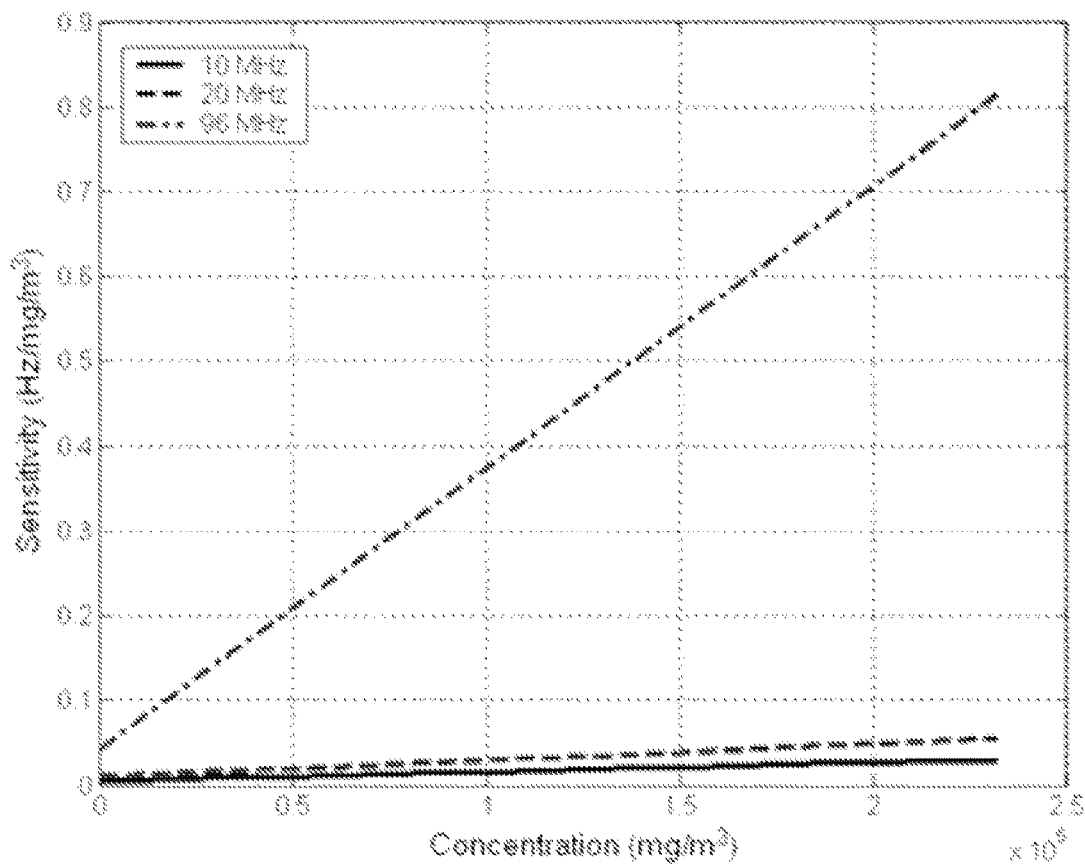

FIG. 7 shows the calibration and device sensitivity plots as functions of vapor phase concentration for the three sensors studied. The device sensitivity is the first derivative of the calibration curve, and is simply the change in device frequency per unit change in vapor phase concentration. The calibration curves are represented very well by a quadratic function of the form $$\Delta f = aC^2 + bC \quad (13)$$

Where $\Delta f$ is the frequency shift that results from solvent exposure, and C is the vapor phase concentration of the analyte. Parameters for these regressions are given in Table 4.

TABLE 4

Sensor calibration equation parameters

| Sensor Device | A | B | Regression Coefficient |
|---|---|---|---|
| 10MHz | 5.390×10$^{-8}$ | 5.439×10$^{-3}$ | 0.9974 |
| 20MHz | 9.839×10$^{-8}$ | 1.008×10$^{-3}$ | 0.9976 |
| 96MHz | 1.661×10$^{-6}$ | 4.280×10$^{-2}$ | 0.9921 |

Device sensitivity is seen to be linear in concentration, with a larger slope for the 96 MHz device indicating that this device can be utilized very well as a process monitor for higher concentrations of analyte, in addition to being useful as a low concentration detector (such as in lower explosion limit detection safety applications). Note that the device sensitivity of the 96 MHz sensor is 7.9 times that of the 10 MHz device at the lowest end of the concentration range, and is nearly 27 times that of the 10 MHz device at the highest concentration studied (2.33×10$^5$ mg/m$^3$). The device sensitivity ratio can be estimated from Sauerbrey's model to be a factor of 92 times the ratio of the film thicknesses, which are 961 and 141 nm, for the 10 and 96 MHz devices, respectively. This yields a constant value of 13.5 across the concentration range. In contrast, the observed values vary from 7.9 to 27. Part of the discrepancy at the lower concentration end can be explained by the uncertainty in determining the polymer film thickness, especially on the 96 MHz device. At the higher end, it is the deviation of the device response characteristics from Sauerbrey's model (viscoelastic effects) for the 96 MHz device that likely explain the difference. Given the much thinner quartz thickness of the 96 MHz device, it is difficult to achieve much larger areal mass densities of the polymer (coating thicknesses) without damping out the response. We have found that the poly(isobutylene) film thickness can at most be increased by an additional 30% without damping out the device. Hence, it should be accepted that the improvements to device sensitivities for the higher frequency TSM devices will be factors of 10 to 40 compared to the lower frequency devices for organic vapor sensing applications. This is indeed a significant improvement, with further optimization at an intermediate frequency possible. Larger thicknesses of polymer coatings could also come with the penalty of increased response and recovery times, due to slow diffusion of solvents in polymers.

3.3 Limit of Detection

The limit of detection (L.O.D.) and the noise level for each resonator were also determined from the sensor responses. Similar to the baseline drift, the frequency noise increased with the fundamental frequency of the resonators. The frequency noise is important since it determines the detection limit for the sensor. The frequency noise was defined as three times the standard deviation (S.D.) of the mean resonant frequency taken over a 7 minute interval in the presence of 100 sccm of pure nitrogen gas flow. L.O.D., signal noise, and baseline drift for each resonator are given in Table 5. The limiting slopes at zero vapor concentration (intercepts of the sensitivity lines in FIG. 7) were utilized in determining L.O.D.

TABLE 5

Comparison of sensor drift, noise and LOD

| Resonator (MHz) | Total baseline drift (Hz/220 min) | Noise (Hz, 3S.D. mean signal) | L.O.D. (mg/m$^3$, 3Noise/Cp) |
|---|---|---|---|
| 9.98 | 49 | 0.444 | 245 |
| 19.97 | 260 | 0.900 | 268 |
| 96.89 | 2342 | 3.650 | 256 |

The noise level for the 96 MHz resonator was considerably higher than that of the 10 MHz resonator. Consequently, the L.O.D. did not improve despite the improvement in the sensitivity of higher fundamental frequency resonators. It is typical and expected that higher sensitivity physical structures are prone to higher baseline noise leading to lower L.O.D.s. It is likely that the inert nitrogen gas flow is the cause for the environmental perturbations that lead to the baseline noise. Indeed, noise levels were found to be considerably lower for this higher frequency device in a static environment. In a lower explosion limit or other detection application, air flow over the device is minimal and lower L.O.D.s can be realized in practical devices. Another source of noise is likely from the electrical interference on these devices, which will be further minimized in a circuit board mounted device driven using an oscillator circuit.

Considering that the noise levels in a flowing stream are similar in magnitude at all exposure concentrations, and putting this together with nearly 30-fold increase in sensitivity at higher concentrations, we can conclude that the higher fundamental frequency devices will make good process monitors. High sensitivity leading to high accuracy is desirable for process control applications. By dilutions using an inert gas supply, the dynamic range can be expanded to arbitrarily higher concentrations in the analyzed gas stream.

3.4 Response and Recovery Times

Figure 8A:
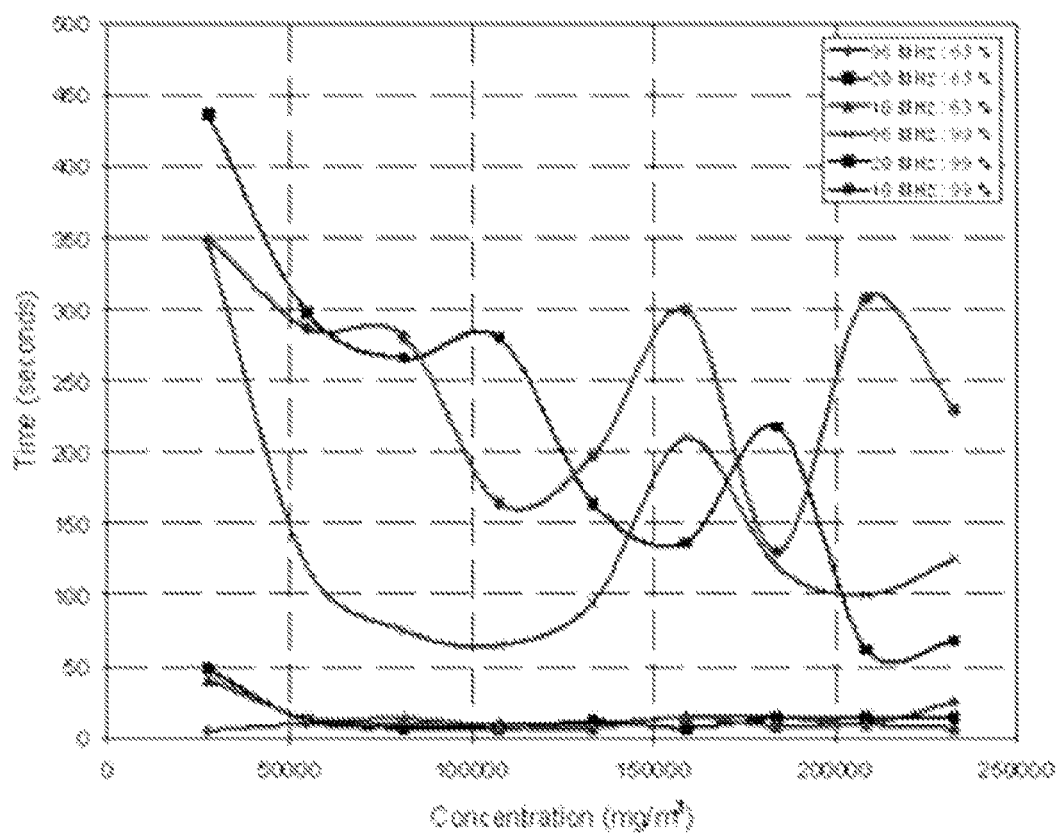
FIG. 8 is a graph illustrating the (A) response and (B) recovery times for the three sensors as functions of vapor phase concentration.
Figure 8B:
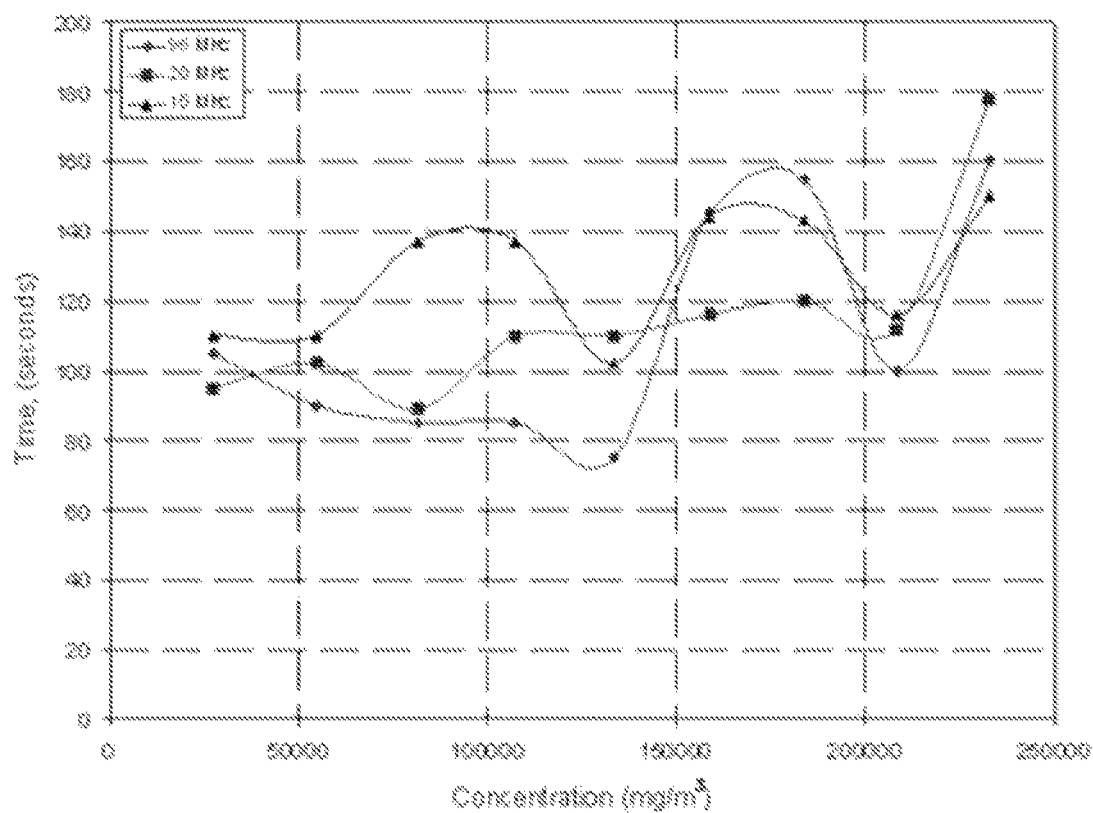
Figure 9:
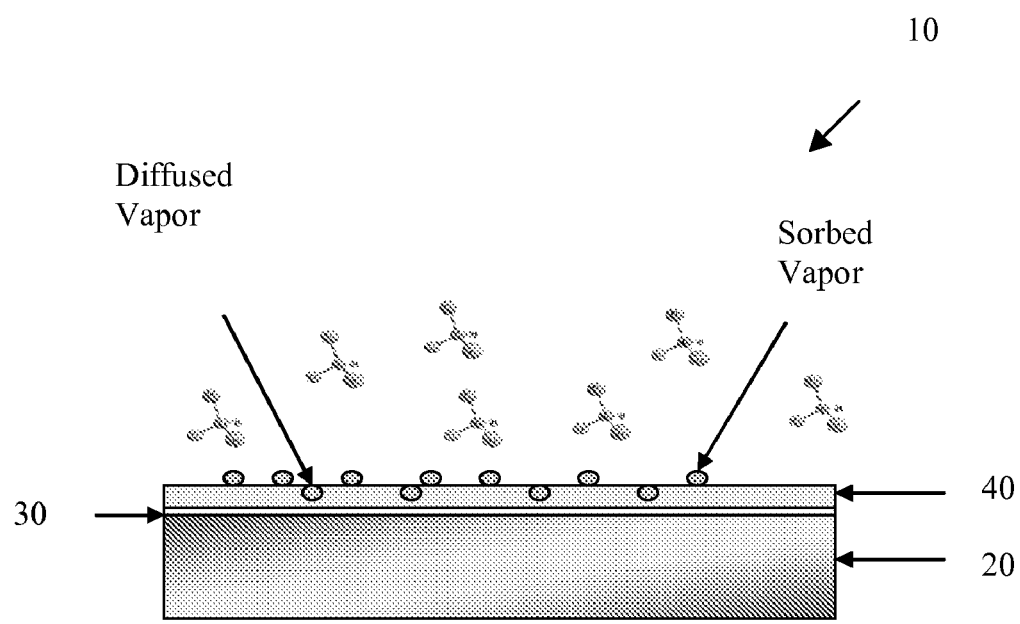
FIG. 9 is an illustration of a TSM sensor used to sense a vapor where the TSM sensor has a quartz layer (lower), an electrode (middle layer) and a polymer layer (upper layer in illustrated resonator).
Figure 10:
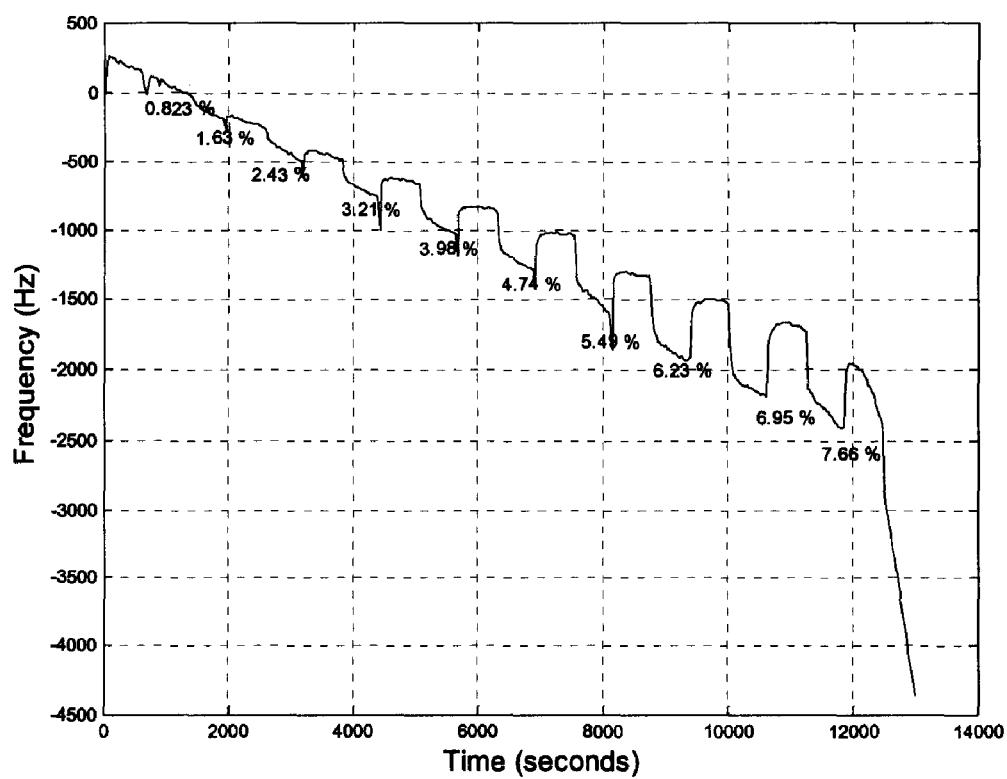
FIG. 10 is a graph showing the 20 MHz response to benzene of a TSM sensor utilizing a PVA film.

Sensor frequency shift did not follow an exponential decay with time, hence, response time constants using fits to an exponential function could not be made. Instead, a value for the full response was established from a criterion of fluctuations around a mean value, and time constants for 63%, 95% and 99% sensor response were calculated. The 63% and 99% response times as well as the 99% recovery times are shown in FIG. 8. The 63% response time is between 10 and 20 seconds for all three sensors, except at the lowest concentration tested, where, the higher frequency device responds more quickly. The 99% response times also show a decreasing trend with concentration for all devices, with the 96 MHz device showing smaller times. These results are consistent with unsteady-state diffusion behavior in a polymer slab, however, smooth and monotonic decrease of the response times with increasing benzene concentration is not seen. This could be due to the non-uniform nature of the polymer film, and the complex nature of the diffusion process in these films. Recovery is relatively quick (FIG. 8.*b*), with 100 to 180 seconds for 99% recovery seen for all devices over the concentration range studied, with the 96 MHz device recovering quicker than the lower frequency devices.

3.5 Alternative Polymer Films

Figure 11:
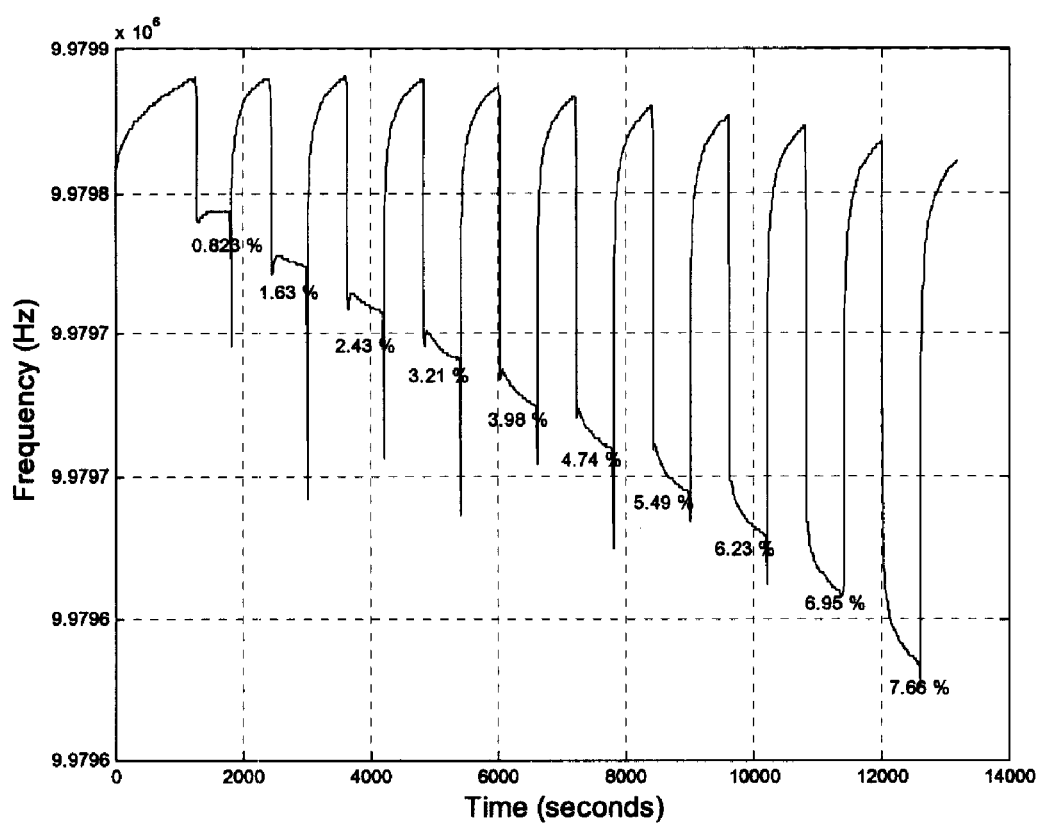
FIG. 11 is a graph showing the 10 MHz response to benzene of a TSM sensor utilizing a PVP film.

Several polymer films were utilized for sensing organic vapors. These polymers were polyvinyl acetate, polyvinyl pyrrolidone, polyisobutylene, polystyrene, polystyrenebutadiene copolymers. An ideal sensing film should be able to recover after exposure to the analyte, have a stable baseline frequency, and repeatable responses. These features are affected by the properties of the polymer. Mainly the film should be rigid enough to move with the oscillation of the TSM resonator, but the film should also be soft enough to allow for sorption of the analyte. Films that are too rigid have longer equilibrium times, consequently, these films may not be practical for a sensing application. Equilibrium times of less than one minute are ideal. Polystyrene, polyvinyl acetate, and polyvinyl pyrrolidone films were found to have equilibrium times of more than 20 minutes when exposed to 27,000 mg/m3 of benzene at room temperature. FIG. 11 shows a typical response of a 20 MHz TSM resonator coated with 23.25 kHz of polyvinyl acetate (PVA) to benzene vapors (0.823 to 7.66 volume percentages). Notice that the resonator frequency continuously decreases and that an equilibrium is never reached for all exposure levels. This response is typical of a film that has a long equilibrium time and does not readily desorb the analyte. A similar response was obtained with polyvinyl pyrrolidone (PVP) coated to 20.03 kHz on a 10 MHz resonator (FIG. 11). Hence, polystyrene would not be an ideal film for sensing benzene. Polymer films of polybutadiene were too soft, resulting in unstable baseline frequencies, large baseline drifts, and poor repeatability.

The polymer glass transition temperature was found to be factor which determined whether a film would behave ideally. Glass transition temperatures of the polymers investigated in this work are presented in Table 6. The temperature at which sensing occurs should be above the glass transition temperature of the polymer for equilibrium times to be low. This is because the as the temperature increases the thermal energy in the polymer solvent system is sufficient to overcome molecular forces between the polymer, allowing for sorption. However, too low of a glass transition temperature resulted in a polymer film that was difficult to coat onto the TSM resonators. Additionally, as the polymer sorbs the analyte, properties of the polymer change. In particular the glass transition temperature becomes depressed, depending upon the concentration of the analyte. This is because the analyte has a lubricating effect on the polymer and causes the individual chains in the polymers to move more freely. The net effect is a plasticization of the polymer and a depression of the glass transition temperature. Changes in the shear modulus of the polymer also result from sorption. This is because the viscoelastic properties of the polymer changes in response to the sorbed vapor. The shear modulus is directly related to the rigidness of the polymer and the intermolecular forces within the polymer. Consequently, as these forces change due to sorption, the shear modulus also changes. The motional resistance of the TSM resonator increases as the polymer film becomes softened. This change in the motional resistance can be used to determine the shear modulus. Since the extent of change in the viscoleastic properties of the film varies according to the quantity and identity of the organic vapor, it was possible to distinguish between the organic vapors by monitoring the motional resistance of the TSM resonator.

TABLE 6

| Polymer | $T_g$ (°C.) |
|---|---|
| Polybutadine | −102 |
| Polyisobutylene | −76 |
| Polystyrene | 60-93 |
| Polyvinylacetate | 30 |
| Polyvinylpyrrolidone | 160 |

4. CONCLUSIONS

Milled TSM resonators with increased fundamental resonant frequencies can be utilized as improved organic vapor sensors both in a detection mode and in process stream monitoring applications. Significant improvements to the device sensitivity are realized compared to the lower frequency devices. Sensitivity was found to be analyte concentration dependent. Further improvements to sensitivity were found not to be possible due to damping out of the response from the higher frequency devices at higher sensing film thicknesses. L.O.D. for the higher frequency device was found to be comparable to the lower frequency devices. Response times were shorter for the higher frequency device, with a decreasing trend with analyte concentration for all devices. Recovery times were small for all devices and increased with analyte concentration. These TSM devices coated with rubbery polymers were found to exhibit adequately fast response and recovery times. Sensor frequency response magnitudes compared reasonably well with the perturbation model of Sauerbrey, with larger deviations observed at higher vapor concentrations. Fragility of the milled device was found not to be a significant issue with properly designed polymer coating procedures. With further optimization of device frequency and polymer film thickness, viable organic vapor sensors are possible for detection and process monitoring applications using higher frequency TSM devices. These devices have advantages of simpler electronics, easier design and fabrication, well-developed models and good baseline stability compared to other acoustic wave devices.

REFERENCES

[1] G. Frye-Mason, R. Kottenstette, P. Lewis, E. Heller, R. Manginell, D. Adkins, G. Dulleck, D. Martinez, D. Sasaki, C. Mowry, C. Matzke, L. Anderson, Hand-held miniature chemical analysis system μChemLab) for detection of trace concentrations of gas phase analytes, Micro Total Analysis Systems 2000, 3 (2000) 229.

[2] C. Lu, A. W. Czanderna, Applications of piezoelectric quartz crystal microbalances, Amsterdam, Elsevier. 7 (1984)

[3] T. Nakamoto, Identification capability of odor sensor using quartz-resonator array and neural-network pattern recognition, Sensors and Actuators B: Chemical, 1 (1990) 473-476.

[4] T. Nakamoto, Odor recorder for multi-component odor using two-level quantization method, Sensors and Actuators B: Chemical, 89 (2003) 120-125.

[5] T. Nakamoto, Improvement of odor-recorder capability for recording dynamical change in odor, Sensors and Actuators B: Chemical, 99 (2004) 367-372.

[6] M. D. Ward, L. Zuxuan, C. M. Yip, I. S. Joseph, Operation of an ultrasensitive 30 MHz quartz microbalance in liquids, Anal. Chem., 65 (1993) 1546-1551.

[7] G. Sauerbrey, The use of quartz oscillators for weighing thin films and for microweighing, Zeitschrift fur Physik, (1959) 206-222.

[8] E. Uttenthaler, M. Schraml, J. Mandel, S. Drost, Ultrasensitive quartz crystal microbalance sensors for detection of M13-phages in liquids, Biosensors and Bioelectronics, 16 (2001) 735-743.

[9] D. S. Ballantine, R. M. White, S. J. Martin, A. J. Ricco, E. T. Zellers, G. C. Frye, H. Wohltjen, Acoustic wave sensors: theory, design, and physico-chemical applications, Academic Press, San Diego, 1997.

[10] D. A. Neumeier, Chemical milling of quartz using a solution based on organic solvents and anhydrous hydrofluoric acid, 2002 IEEE International Frequency Control Symposium and PDA Exhibition (2002) 394-402.

[11] J. R. Hunt., R. C. Smythe, Chemically milled VHF and UT-IF AT-cut resonators, In Proceedings of the 39th Annual Frequency Control Symposium (1986) 292-300.

[12] J. R. Vig, J. W. Lebus, R. L. Filler, Chemically polished quartz, Proc. on the 31s Annual Symposium on Frequency Control (1977) 131-143.

[13] R. W. Ward, Etching of quartz crystal spheres, Salt Lake City, Utah, 1993 IEEE International Frequency Control Symposium (1993) 390-396.

[14] J. R. Vig, J. Ballato, R. E. Riman, S. Laffey, Etching Quartz Crystals in Anhydrous HF Gas, 1996 IEEE International Frequency Control Symposium (1996) 201-208.

[15] G. K. Guttwein, A. D. Ballato, T. J. Lukaszek, VHF-UHF Piezoelectric Resonators. U.S. Pat. No. 3,694,677, USA, (1972)

[16] R. S. Barratt, The Preparation of Standard Gas Mixtures, A Review, The Analyst, 106 (1981) 817-849.

[17] J. W. Grate, D. S. Ballantine, H. Wohltjen, An automated vapor generation and data collection instrument for the evaluation of chemical microsensors, Sensors and Actuators, 11 (1987)173-188.

[18] G. O. Nelson, Gas Mixtures: Preparation and Control, Lewis Publishers, New York, 1992.

[19] R. C. Reid, J. M. Prausnitz, B. E. Poling, The Properties of Liquids and Gases, McGraw Hill, New York, 1987.

[20] W. Hao, H. S. Elbro, P. Alessi, Polymer Solution Data Collection, DECHEMA, Frankfurt, 1992.

[21] J. W. Grate, S. N. Kaganove, V. R. Bhethanabotla, Examination of mass and modulus contributions to thickness shear mode and surface acoustic wave vapor sensor responses using partition coefficients, Faraday Discussion, 107 (1997) 259-283.

[22] J. W. Grate, A. R. McGill, Dewetting effects on polymer coated surface acoustic wave vapor sensors, Anal. Chem., 67 (1995) 4015-4019.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described, What is claimed is:

1. A thickness shear mode (TSM) gas and organic vapor sensor comprising:
a quartz crystal having an oscillating region of reduced thickness surrounded by an outer region, wherein the outer region is comparatively thicker than the oscillating region and the oscillating region has an operating frequency greater than about 50 Mhz;
a first electrode positioned on a first side of the quartz crystal;
a second electrode, having approximately the same size and shape as the first electrode, positioned on a second side of the quartz crystal;
a first polymer sensing film in contact with the oscillating region of the quartz crystal on the first side of the quartz crystal and further in contact with the first electrode; and
a second polymer sensing film in contact with the oscillating region of the quartz crystal on the second side of the quartz crystal and further in contact with the second electrode.

2. The TSM sensor according to claim 1 wherein the operating frequency of the polymer coated resonator is about 96 MHz.

3. The TSM sensor according to claim 1, wherein the polymer is selected from the group consisting of viscoelectric polymers, polyvinyl acetate, polyvinyl pyrrolidone, polyisobutylene, polystyrene, and polystyrenebutadiene.

4. The TSM sensor according to claim 1, wherein the thickness of the first polymer sensing film is about equal to the thickness of the second polymer sensing film.

5. The TSM sensor according to claim 1, wherein the ratio of the diameter of the outer region of the quartz crystal to the diameter of the oscillating region is about 0.1.

6. The TSM sensor according to claim 1, wherein the thickness of the outer region of the quartz crystal is about 50 micrometers and the thickness of the oscillating region is about 17 micrometers.

7. The TSM sensor according to claim 1, wherein the ratio of the thickness of the polymer sensing film to the thickness of the oscillating region is about 0.01.

8. A method of gas or vapor sensing in an analyte comprising the steps of:
- providing a quartz crystal having an oscillating region of reduced thickness surrounded by an outer region, wherein the outer region is comparatively thicker than the oscillating region and the oscillating region has an operating frequency greater than about 50 Mhz;
- positioning a first electrode on a first side of the quartz crystal;
- positioning a second electrode, having approximately the same size and shape as the first electrode, on a second side of the quartz crystal;
- positioning a first polymer sensing film in contact with the oscillating region of the quartz crystal on the first side of the quartz crystal and further in contact with the first electrode;
- positioning a second polymer sensing film in contact with the oscillating region of the quartz crystal on the second side of the quartz crystal and further in contact with the second electrode to form a TSM organic gas or vapor sensor;
- contacting the TSM sensor with the analyte; and
- measuring the frequency shift of the sensor upon contact with the analyte wherein a frequency shift is indicative of the presence or concentration in the analyte of the gas or vapor to be sensed.

9. The method according to claim 8 wherein the gas or vapor is an organic gas or vapor.

10. The method according to claim 8 wherein the gas or vapor is selected from the group consisting of benzene, hexane, cyclohexane, heptane, dichloroethane, chloroform, and toluene.

11. The method according to claim 8 wherein the gas or vapor is benzene.

12. The method according to claim 8 wherein the operating frequency of the polymer coated resonator is about 96 MHz.

13. The method according to claim 8, wherein the polymer of the TSM organic gas or vapor sensor is selected from the group consisting of viscoelectric polymers, polyvinyl acetate, polyvinyl pyrrolidone, polyisobutylene, polystyrene, and polystyrenebutadiene.

14. The method according to claim 8, wherein the thickness of the first polymer sensing film of the TSM organic gas or vapor sensor is about equal to the thickness of the second polymer sensing film of the TSM organic gas or vapor sensor.

15. The method according to claim 8, wherein the ratio of the diameter of the outer region of the quartz crystal to the diameter of the oscillating region is about 0.1.

16. The method according to claim 8, wherein the thickness of the outer region of the quartz crystal is about 50 micrometers and the thickness of the oscillating region is about 17 micrometers.

17. The method according to claim 8, wherein the ratio of the thickness of the polymer sensing film to the thickness of the oscillating region is about 0.01.

* * * * *